(12) United States Patent
Dan et al.

(10) Patent No.: US 10,588,498 B2
(45) Date of Patent: Mar. 17, 2020

(54) VIDEO LARYNGOSCOPE SYSTEMS

(71) Applicant: Truphatek International Ltd., Netanya (IL)

(72) Inventors: Gabriel Dan, Tel Aviv (IL); David Rosenblatt, Beer Sheva (IL)

(73) Assignee: TRUPHATEK INTERNATIONAL LTD, Netanya (IL)

( * ) Notice: Subject to any disclaimer, the term of this patent is extended or adjusted under 35 U.S.C. 154(b) by 0 days.

(21) Appl. No.: 14/891,137

(22) PCT Filed: May 15, 2014

(86) PCT No.: PCT/IL2014/050426
§ 371 (c)(1),
(2) Date: Nov. 13, 2015

(87) PCT Pub. No.: WO2014/184795
PCT Pub. Date: Nov. 20, 2014

(65) Prior Publication Data
US 2016/0095506 A1    Apr. 7, 2016

(30) Foreign Application Priority Data

May 16, 2013    (IL) .......................................... 226379

(51) Int. Cl.
A61B 1/05       (2006.01)
A61M 16/04      (2006.01)
(Continued)

(52) U.S. Cl.
CPC ............ *A61B 1/051* (2013.01); *A61B 1/0005* (2013.01); *A61B 1/00039* (2013.01); *A61B 1/00052* (2013.01); *A61B 1/045* (2013.01); *A61B 1/05* (2013.01); *A61B 1/267* (2013.01); *A61M 16/0488* (2013.01)

(58) Field of Classification Search
CPC .......... A61B 1/24; A61B 1/267; A61B 1/2673; A61B 1/2676; A61B 1/273; A61B 1/2733
See application file for complete search history.

(56) References Cited

U.S. PATENT DOCUMENTS 5,800,344 A      9/1998  Wood, Sr. et al.
6,139,491 A  * 10/2000  Heine ...................... A61B 1/07
                                                              600/190

(Continued)

FOREIGN PATENT DOCUMENTS

WO        2012172076 A1    12/2012

OTHER PUBLICATIONS

European Search Report issued in European Patent Application No. 14798319.1 dated Jan. 11, 2017.

*Primary Examiner* — Lynnsy M Summitt
(74) *Attorney, Agent, or Firm* — Baker & Hostetler LLP

(57) ABSTRACT

Video laryngoscope system including a video laryngoscope having a laryngoscope handle and a laryngoscope blade. The video laryngoscope system includes an image capture module with at least two stationary imaging units spaced apart along the laryngoscope blade for providing real-time video streams of a patient's airway passage during an intubation and a controller for enabling a clinician performing the intubation to select one or more of the real-time video streams for real-time display on a display screen to assist intubation of a patient.

17 Claims, 4 Drawing Sheets

(51) Int. Cl.
*A61B 1/267* (2006.01)
*A61B 1/045* (2006.01)
*A61B 1/00* (2006.01)

(56) References Cited

U.S. PATENT DOCUMENTS

| | | | | |
|---|---|---|---|---|
| 6,840,903 B2* | 1/2005 | Mazzei | ................... | A61B 1/267 600/185 |
| 8,398,545 B2 | 3/2013 | Chen et al. | | |
| 8,419,634 B2* | 4/2013 | Nearman | ............. | A61B 1/00041 600/188 |
| 8,460,184 B2* | 6/2013 | Nearman | ................ | A61B 1/267 600/188 |
| 8,652,033 B2* | 2/2014 | Berci | ................... | A61B 1/0005 600/185 |
| 8,814,787 B2* | 8/2014 | Menegazzi | .......... | A61B 1/0008 600/190 |
| 8,827,899 B2* | 9/2014 | Farr | ................... | A61B 1/00052 600/188 |
| 8,894,569 B2* | 11/2014 | Qiu | ................... | A61B 1/00009 128/200.26 |
| 9,326,669 B2* | 5/2016 | Nearman | ................ | A61B 1/267 |
| 9,332,896 B2* | 5/2016 | Patel | ................... | A61B 1/00096 |
| 2005/0279355 A1* | 12/2005 | Loubser | ............. | A61B 1/00103 128/200.26 |
| 2006/0020171 A1* | 1/2006 | Gilreath | ............. | A61B 1/00105 600/188 |
| 2007/0179342 A1* | 8/2007 | Miller | .................... | A61B 1/267 600/188 |
| 2008/0064926 A1* | 3/2008 | Chen | .................. | A61B 1/00016 600/110 |
| 2008/0177146 A1* | 7/2008 | Chen | ....................... | A61B 1/267 600/185 |
| 2010/0081875 A1* | 4/2010 | Fowler | ............... | A61B 1/00149 600/114 |
| 2010/0198009 A1* | 8/2010 | Farr | ................... | A61B 1/00103 600/109 |
| 2011/0137127 A1* | 6/2011 | Schwartz | ........... | A61B 1/00052 600/188 |
| 2011/0263935 A1 | 10/2011 | Qiu | | |
| 2012/0078055 A1* | 3/2012 | Berci | ................... | A61B 1/0005 600/188 |
| 2012/0116156 A1 | 5/2012 | Lederman | | |
| 2012/0190929 A1 | 7/2012 | Patel et al. | | |
| 2014/0194684 A1* | 7/2014 | Raymondos | ......... | A61B 1/0008 600/109 |
| 2015/0080655 A1* | 3/2015 | Peterson | ............ | A61B 1/00009 600/112 |

* cited by examiner

VIDEO LARYNGOSCOPE SYSTEMS

CROSS-REFERENCE TO RELATED APPLICATIONS

This application is a National Stage Application of International Application No. PCT/IL2014/050426, filed on May 15, 2014, which claims priority to foreign Israel Patent Application No. IL 226379, filed on May 16, 2013, the disclosures of which are incorporated by reference in their entirety.

FIELD OF THE INVENTION

The present disclosure is directed toward video laryngoscope systems.

BACKGROUND OF THE INVENTION

Video laryngoscopy for assisting tracheal intubation is a commonplace medical procedure alongside traditional direct view laryngoscopy and indirect view laryngoscopy using optical view tubes. Tracheal intubation can be further facilitated by the use of a video stylet in conjunction with a video laryngoscope.

Video laryngoscopy includes a handheld video laryngoscope and a display screen for instantaneously displaying an anatomically defined sequence of progressively imaged physiological structures during the manipulation of a laryngoscope blade from an initial blade insertion into a patient's mouth to a final blade position for assisting tracheal intubation. The anatomically defined sequence of progressively imaged physiological structures includes the following intubation significant landmarks: (1) the tongue and uvula, (2) the epiglottis, (3) the posterior cartilages and interarytenoid notch, (4) the glottic opening, and (5) the vocal cords.

Challenges often arise to hinder recognition of progressively imaged physiological structures. For example, recognition of the epiglottis may be hindered owing to its visual similarity to the mucosa of the posterior pharynx, and accumulation of blood, secretions, and/or vomitus in the posterior pharynx. Improper identification of certain landmarks can lead to errors in intubations. For example, if the esophagus and glottic opening are confused, esophageal, rather than tracheal, intubation may occur.

US Patent Application Publication No. US 2012/0190929 to Patel et al. (hereinafter the Patel disclosure) discloses a laryngoscope including a handle, a blade holding element, a detachable blade, means for viewing the laryngeal inlet of a patient and means for adjusting the viewing field. The Patel disclosure discloses the laryngoscope is configured to be usable with at least two different detachable blades including inter alia straight blades, curved blades, and so-called difficult intubation blades.

Patel paragraph [0013] discloses a blade holding element with a multi-camera system including two adjacent fixed cameras directed to two different viewing fields and intended to be used with different blades. Patel paragraph [0013] also discloses means for switching from one camera to the other so that a clinician may select to use the first camera for when the laryngoscope is fitted with a standard blade and the second camera when a difficult intubation blade is used.

Patel paragraph [0014] discloses a blade holding element with a single movable or tiltable camera and mechanical or electronic means for remotely changing the position of the camera for positioning in a desired position to provide a clear, non-distorted view of a patient's laryngeal inlet.

U.S. Pat. No. 5,800,344 to Wood, Sr. et al, (hereinafter the Wood disclosure) discloses a video laryngoscope having an image sensor assembly mounted thereon for providing video imaging of a patient's airway passage. The Wood disclosure discloses a fixed position image sensor and an image sensor assembly slidably mounted on a track formed on a curved section of a laryngoscope body so that sliding of the image sensor assembly along the track adjusts the distance of the assembly from a target and the orientation angle of the image sensor assembly.

U.S. Pat. No. 8,398,545 to Chen et al. (hereinafter the Chen disclosure) discloses a video laryngoscope with a movable image capturing unit similar to the Wood disclosure. The Chen disclosure discloses a laryngoscope with a side mounted display and also a laryngoscope with an external display for reducing the volume and size of the laryngoscope.

U.S. Pat. No. 8,652,033 to Berci et al. (hereinafter the Berci disclosure) discloses a video intubation system that provides multiple streams to be simultaneously presented to a user. A video laryngoscope provides a first image stream and a video stylet provides a second image stream. The two image streams may be presented to the user on two different side-by-side monitors or a single monitor provided with a split screen. The video intubation system presents a user with a view of the upper portion of a patient's anatomy via the laryngoscope as well as being presented with a view in front of the video stylet as the stylet is advanced through the trachea.

US Patent Application Publication No. US 2011/0263935 to Qiu (hereinafter the Qui disclosure) discloses an intubation system for intubations based on an airway pattern indicating a trachea opening. The airway pattern is determined from analysis of airway data detected by a trachea identifying device disposed on a movable guide stylet of the intubation system. Qui FIG. 4 shows a guide stylet 46 with light sources 62, image capture devices 64a and 64b on either side of a laser pointer 70, gas exchange detectors 66 and control cable 68. Qiu para [0050] discloses the image capture devices may be a video camera to continually capture images or a still camera to capture still images. In another example, the image capture devices may be a thermal camera or an infrared camera to capture thermal images.

US Patent Application Publication No. US 2012/0116156 to Lederman (hereinafter the Lederman disclosure) discloses a medical device includes a tube, at least one imaging sensor coupled to an endoscope in the tube, and a monitor application to monitor positioning of the tube in a medical patient by identifying expected anatomical features in images provided by the at least one sensor. The Lederman disclosure also discloses a method for endotracheal intubation including receiving imaging frames from a sensor located in an endotracheal tube inserted through a patient's and processing the image frames to identify progression of anatomical features consistent with a proper placement of the endotracheal tube. In particular, the Lederman disclosure discloses image processing to identify vocal cords, trachea, the esophagus, carina, and the like.

SUMMARY OF THE INVENTION

The present invention is directed toward video laryngoscope systems including an image capture module with at least two stationary imaging units longitudinally deployed along a laryngoscope blade for generating a corresponding number of different real-time video streams during manipulation of a laryngoscope blade from an initial blade insertion into a patient's mouth to a final blade position for assisting intubations of patients. The present invention is based on the notion that a clinician performing an intubation will be assisted by the ability to select at least one real-time video stream from at least two different real-time video streams at a series of continuous locations of a laryngoscope blade along a patient's airway passage to orient the location of a laryngoscope blade tip in the patient's airway passage and recognize the aforesaid intubation significant landmarks.

The video laryngoscope systems of the present invention include a controller for controlling operation of the imaging module including inter alia real-time video display during intubation procedures, real-time video recording of intubation procedures, and the like. The controller preferably includes user controls which can be readily operated by a clinician performing an intubation, for example, for selecting which one or more real time video streams he wants to be view at a particular instance on a display screen. Such user controls can be preferably provisioned on a laryngoscope handle for finger/thumb operation during an intubation. Alternatively, video laryngoscope systems of the present invention can include touch display screens for touch screen operation similar to a smartphone. Alternatively, one or more real time video streams can be displayed on a display screen in accordance with a default setup which can be overridden by a clinician.

The video laryngoscope systems of the present invention can include image processing software for processing the captured real time video streams prior to their display as disclosed in inter alia the aforementioned Lederman disclosure, the aforementioned Qui disclosure, and the like. Such processing includes inter alia improving contour definition, improving boundary definition, automatic recognition of intubation significant landmarks, and the like.

The video laryngoscope systems of the present invention preferably employ conventional imaging units. Such imaging units preferably include an illumination source, for example, a LED, and the like, for illuminating a patient's airway passage during intubation. Such imaging units include a digital imaging sensor, for example, a CCD, a CMOS chip, and the like. The laryngoscope blades can be provisioned with anti-fogging arrangements for preventing fogging of the digital imaging sensors. One or more of the digital imaging sensors can be tiltable similar to the aforementioned Patel disclosure. Also, the video laryngoscope systems of the present invention can include mechanical or electronic means for remotely changing the tilt of a tiltable digital imaging sensor for positioning in a desired position.

The video laryngoscope systems of the present invention can include a laryngoscope mounted display screen similar to the aforementioned Chen disclosure or an external display screen similar to the aforementioned Berci disclosure. Laryngoscope mounted display screens can be mounted to enable traditional direct view laryngoscopy as well as video laryngoscopy. Alternatively, laryngoscope mounted display screens can be mounted to enable video laryngoscopy only. The display screens can display side-by-side image streams similar to aforementioned Berci disclosure.

Also, as similar to the aforementioned Berci disclosure, the video laryngoscope systems of the present invention can also be used with a video stylet for providing a stylet video stream for display on the display monitor. The video stylets can be re-usable items or disposable single use items. The clinician can select to display a real time video stream from a video stylet on the display screen either by itself or together with a real time video stream from one of the blade mounted imaging units.

The present invention can be readily applied to the differing approaches regarding re-usable components and disposable single use components as exemplified in commercially available video laryngoscope systems. Such commercially available video laryngoscope systems include inter alia the C-MAC by Karl Storz Endovision, Inc., Charlton, Mass., USA, the Glidescope by Verathon, and the like. In some implementations, disposable single use components include electronic sub-components. In other implementations, disposable single use components are employed for sterility purposes only and do not include electronic sub-components. The present invention can also be readily applied to disposable laryngoscope blades for detachable attachment to laryngoscope handles. The disposable laryngoscope blades can be made from metal or plastic. Suitable metal laryngoscope blades are disclosed in commonly assigned U.S. Pat. No. 7,736,304 to Pecherer. Suitable plastic laryngoscope blades are disclosed in commonly assigned U.S. Pat. No. 5,879,304 to Shucman et al.

The video laryngoscope systems of the present invention can be implemented with a wide range of conventional laryngoscope blade shapes and sizes for assisting in regular intubation and so-called difficult intubations. The laryngoscope blade shapes include inter alia Miller blades, Macintosh blades, Foregger-Magill blades, and the like. The laryngoscope blades can be optionally provided with a guide channel for guiding an endotracheal tube.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE INVENTION

Figure 1:
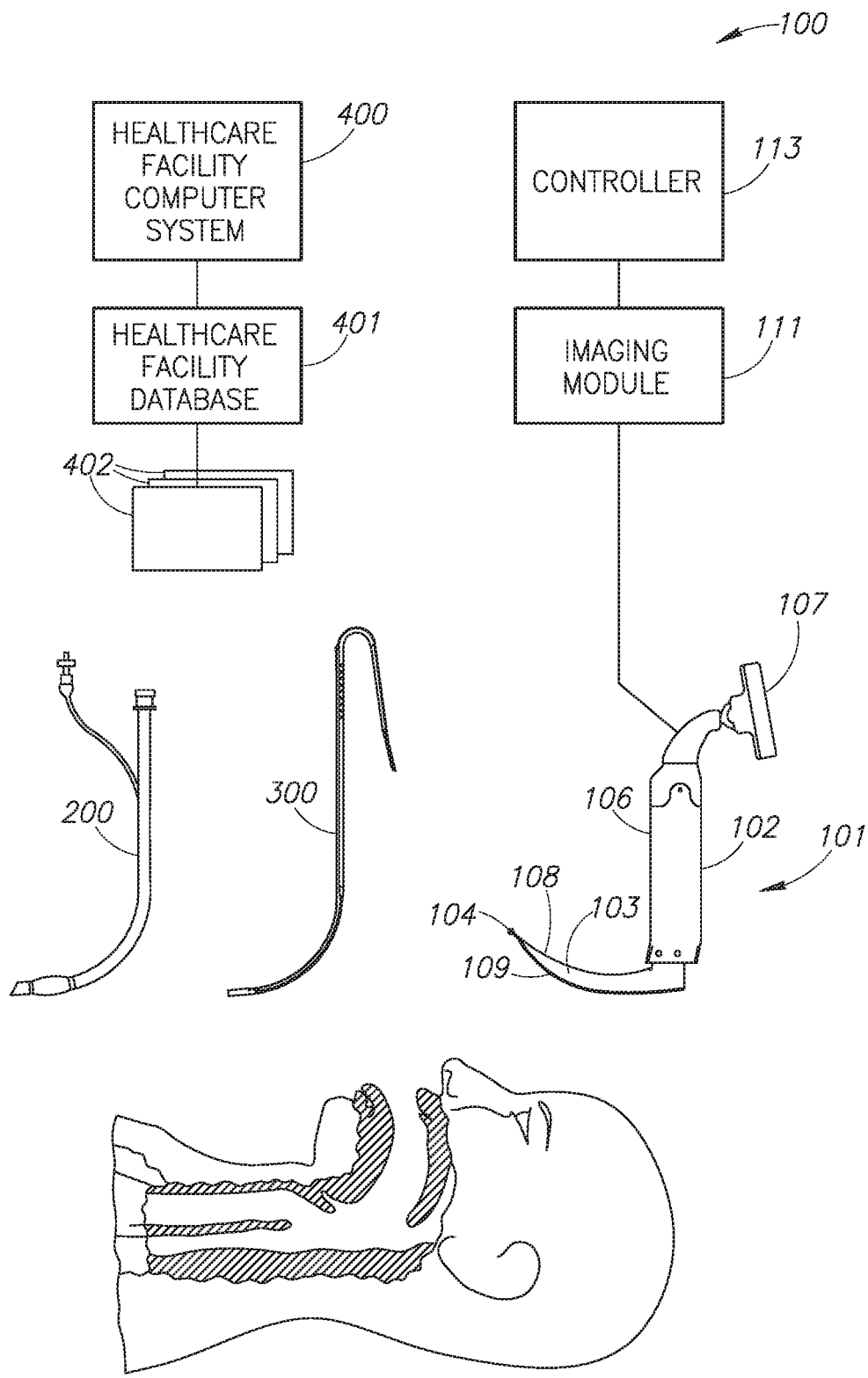
FIG. 1 is a combined pictorial view and block diagram of a video laryngoscope system for use with an endotracheal tube for intubation of a patient.

FIGS. 1 to 5 show a video laryngoscope system 100 for use with an endotracheal tube 200 and a video stylet 300 for assisting tracheal intubations of patients. The video laryngoscope system 100 is preferably in communication with a healthcare facility computer system 400 including a healthcare facility database 401 for storing computer files 402. The video laryngoscope system 100 can generate patient intubation files compatible with standard Electronic Medical Record (EMR) programs. The video laryngoscope system 100 can be in wired or wireless communication with the healthcare facility computer system 400.

The video laryngoscope system 100 includes a handheld video laryngoscope 101 having a laryngoscope handle 102 and a laryngoscope blade 103 transversely extending from the laryngoscope handle 102 and terminating at a distal laryngoscope blade tip 104. The laryngoscope handle 102 includes a power source 106 preferably in the form of a rechargeable battery and an onboard display screen 107. The laryngoscope blade 103 has an underside blade surface 108 for deploying against a patient's tongue on insertion of the laryngoscope blade 103 into his mouth and an upperside blade surface 109 opposite the underside blade surface 108.

The video laryngoscope 101 includes an image capture module 111 including stationary imaging units 112 deployed along the laryngoscope blade 103 at increasing lengths from the distal laryngoscope blade tip 104. The imaging units 112 are each capable of independently and simultaneously generating a real-time video stream of a patient's airway passage during an intubation for selective display on the display screen 107.

The video laryngoscope system 100 includes a controller 113 for controlling the operation of the image capture module 111 including inter alia real-time video display during intubation procedures, real-time video recording of intubation procedures, and the like. The controller 113 can also control the operation of the video stylet 300. The controller 113 is preferably in wireless communication with the video stylet 300.

Figure 2:
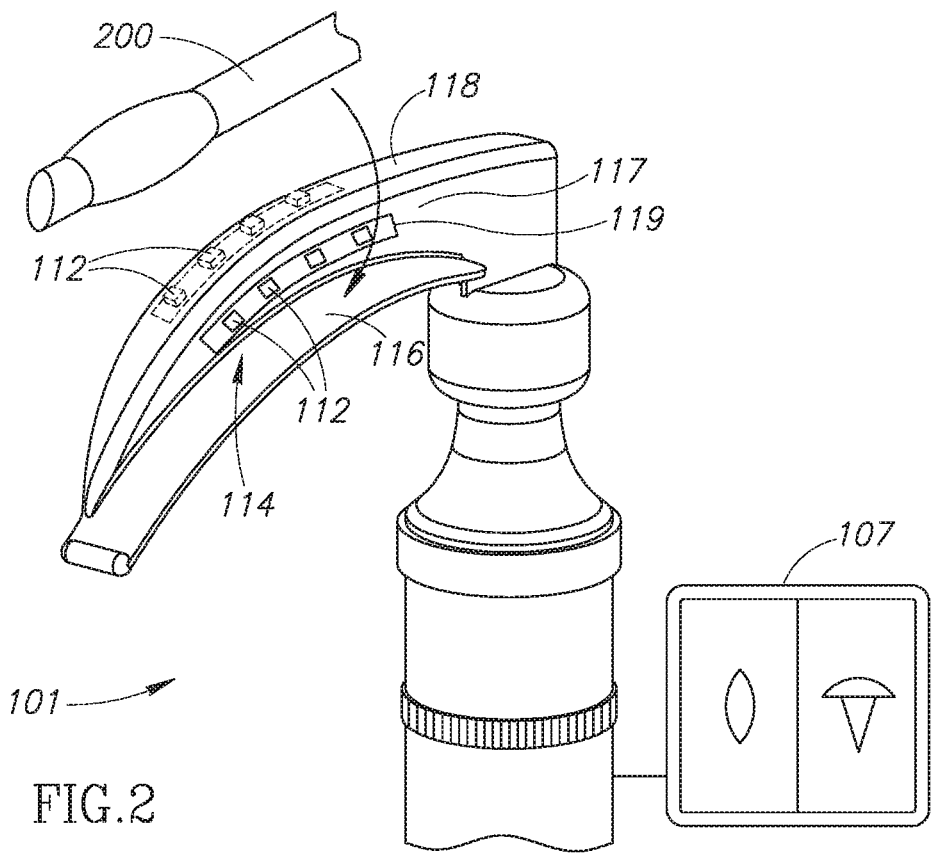
FIG. 2 is a pictorial view of a laryngoscope blade including a daisy chain of four imaging units of an image capture module of a video laryngoscope.

FIG. 2 shows the upperside blade surface 109 has a stepped configuration for forming an elongated guide channel 114 for supporting an endotracheal tube 200 during an intubation. The upperside blade surface 109 includes a major blade surface 116 parallel and opposite the underside blade surface 108, an upright blade surface 117 generally perpendicular to the major blade surface 116 and an uppermost blade surface 118 generally parallel to the major blade surface 116 and tapering theretowards.

The image capture module 111 preferably includes a so-called imaging unit daisy chain 119 of a series of at least two longitudinally spaced apart rigidly mounted imaging units 112 and in this case four imaging units 112 stationary mounted on the laryngoscope blade 103. The imaging unit daisy chain 119 is preferably deployed on the upright blade surface 117. Alternatively, it can be deployed on the uppermost blade surface 118 as shown in dashed lines. The imaging unit daisy chain 119 can be permanently or detachably mounted on the laryngoscope blade 103.

FIG. 2 also shows a display screen 107 remote from the video laryngoscope 101 and simultaneously displaying two different real-time video streams captured by two different imaging units 112.

Figure 3:
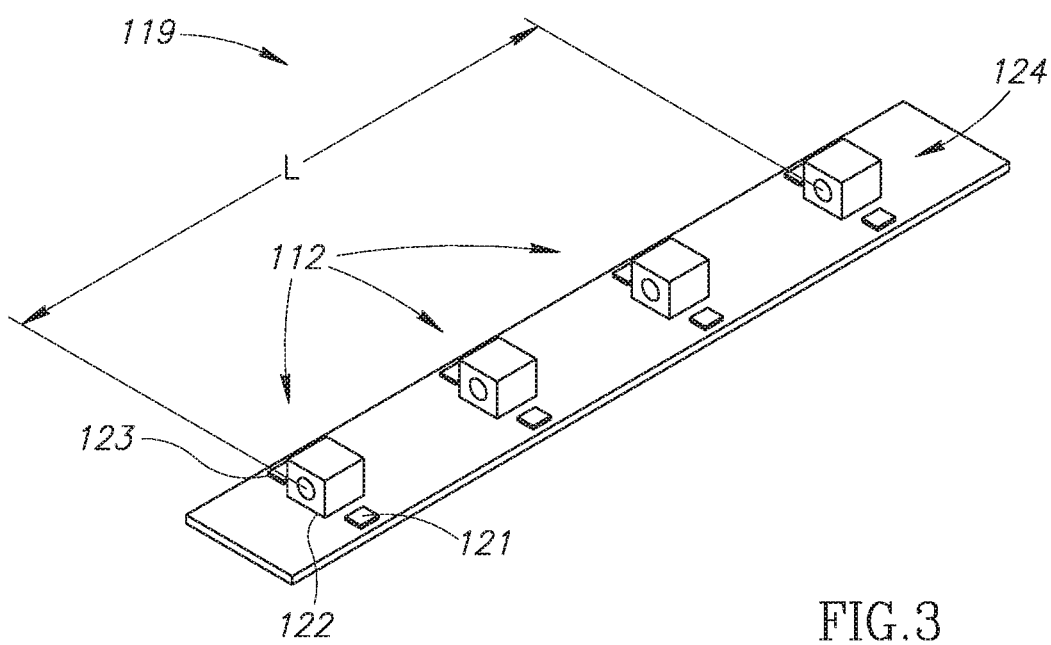
FIG. 3 is an enlarged view of the daisy chain of the image capture module.

FIG. 3 shows each imaging unit 112 includes one or more illumination sources 121 and a digital imaging sensor 122. The digital imaging sensors 122 include inter alia a camera and one or more lenses. An exemplary wafer level CMOS camera is the 1.3M pixel camera cube from Kushan Q Technology Ltd which has a maximum diagonal FOV of 66°. The imaging units 122 can have the same magnification and Field of View (FOV). Alternatively, the imaging units 122 can have different magnifications and FOVs.

Figure 4:
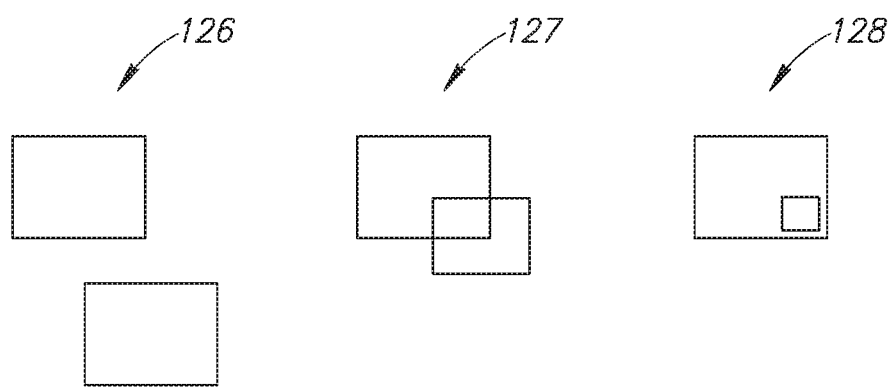
FIG. 4 is a schematic diagram showing three Field Of View (FOV) arrangements of the image capture module.

The image capture module 111 includes at least a pair of imaging units 112 having a leading imaging unit 123 proximate the distal laryngoscope blade tip 104 and a trailing imaging unit 124 behind the leading imaging unit 123 relative to the distal laryngoscope blade tip 104. The length denoted L the trailing imaging unit 124 is behind the leading imaging unit 123 relative to the distal laryngoscope blade tip 104 depends on blade size and is at least 1 cm. In view of their longitudinal spaced apart configuration and the imaging units 123 and 124 can also have different magnifications and therefore different FOVs, FIG. 4 shows three exemplary FOV arrangements as follows: First, the imaging units 123 and 124 have a non-overlapping FOV arrangement 126. Second, the imaging units 123 and 124 have a partially overlapping FOV arrangement 127. And third, the imaging units 123 and 124 have a fully overlapping FOV arrangement 128 with one FOV within the other FOV.

Based on a particular implemented FOV arrangement and taking into account the imaging units 123 and 124 can be at different distances from the internal structures of a patient's airway passage that they are imaging at a particular location of the laryngoscope blade 103 therealong during an intubation, the leading imaging unit 123 and the trailing imaging unit 124 image different sized areas of different locations of a patient's airway passage at a particular location of the laryngoscope blade 103.

Figure 5:
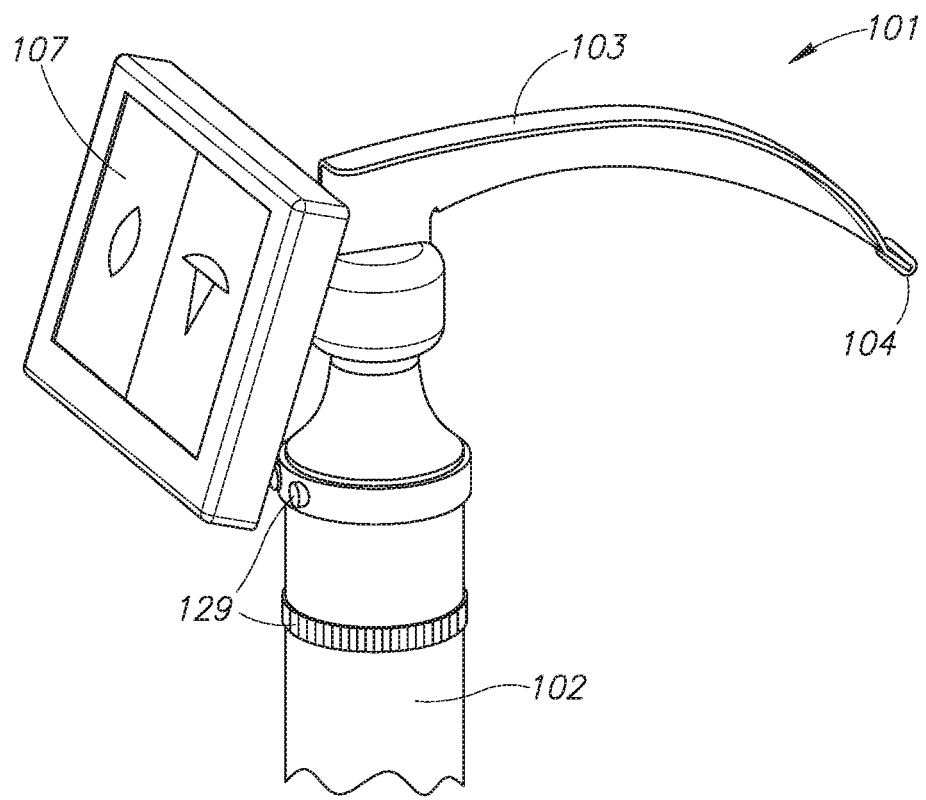
FIG. 5 is a pictorial view of a laryngoscope handle including finger/thumb operated controls.

FIG. 5 shows the controller 113 preferably includes finger/thumb operated controls 129 on the video laryngoscope 101 for enabling a clinician performing an intubation to readily operate the controller 113 to select which one or more real-time video streams he wants to view on the display screen 107 during the intubation. The finger/thumb operated controls 129 can include inter alia push buttons, rotatable thumbscrews, and the like. Also, the display screen 107 can be a touchscreen for touchscreen operation. A clinician can also select to display the real time video stream from the video stylet 300 on the display screen 107. A clinician typically selects to display the real time video stream from the video stylet 300 after the laryngoscope blade 103 is in its final blade position and the clinician has introduced the endotracheal tube 200 along the guide channel 114 thereby obstructing the blade mounted imaging units 112.

The use of a video laryngoscope system 100 with a leading imaging unit 123 and a trailing imaging unit 124 is now described with reference to FIGS. 6A to 6C.

Figure 6A:
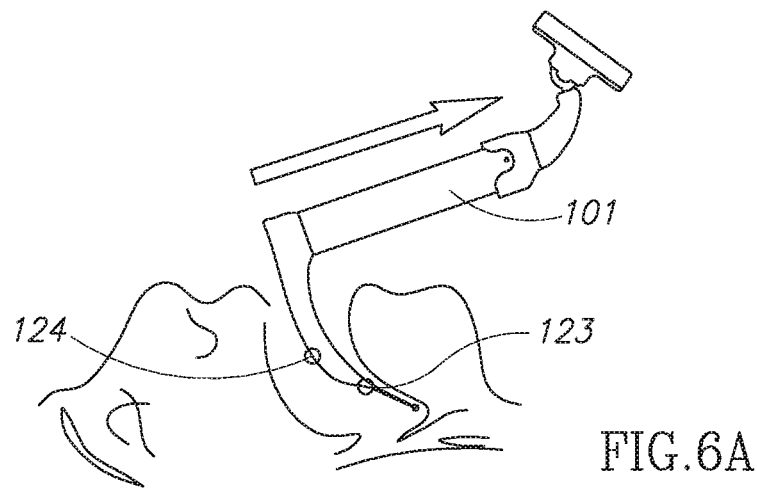
FIGS. 6A to 6C show the use of the video laryngoscope system for assisting an intubation of a patient.

FIG. 6A shows that on initial blade insertion into a patient's mouth, the leading imaging unit 123 obtains a close-up view of the vallecula region of a patient while the trailing imaging unit 124 obtains a view of the patient's uvula and posterior pharynx.

Figure 6B:
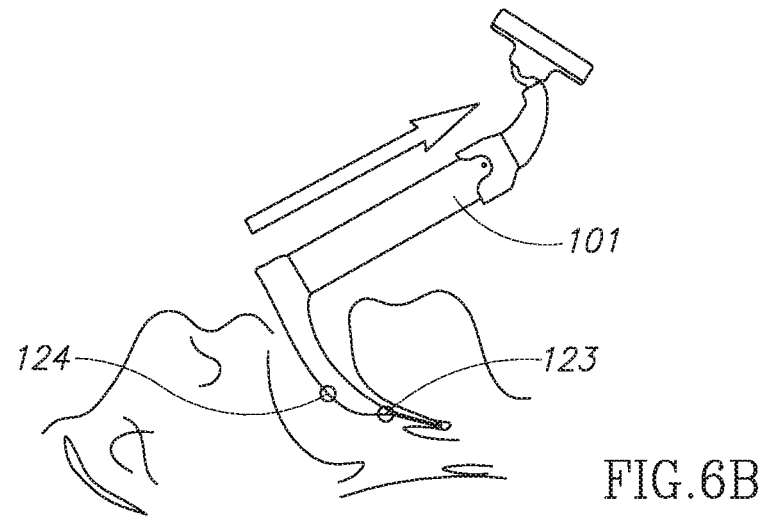

FIG. 6B shows that as the video laryngoscope 101 is advanced down the patient's airway passage, the views obtained by the imaging units change. FIG. 4B shows that as laryngoscope handle 102 is tilted upward, thereby advancing the laryngoscope blade 103, the leading imaging unit 123 is positioned to obtain a close up view of a patient's vocal cords while the trailing imaging unit 124 is positioned to obtain a view of his interarytrnoid notch.

Figure 6C:
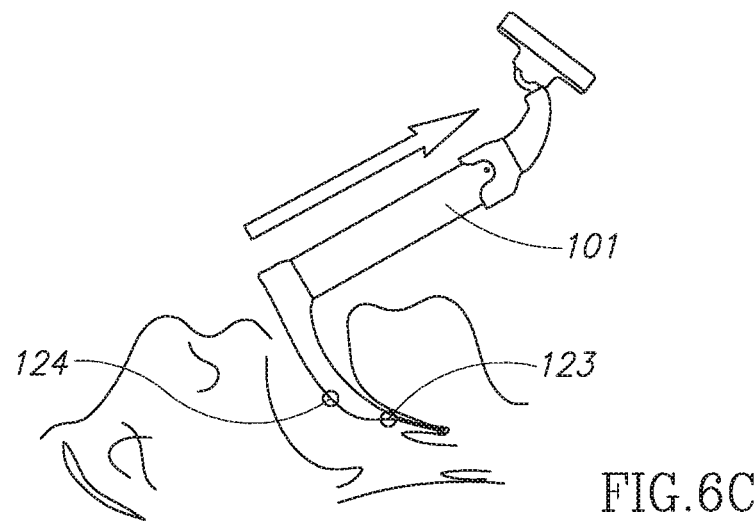

FIG. 6C shows that as the laryngoscope handle 102 is further tilted upward, thereby further advancing the laryngoscope blade 103, the leading imaging unit 123 may be advanced so as to obtain a closer view of vocal cords of the patient, while the trailing imaging unit 124 may be positioned so as to maintain a view of the interarytrnoid notch and the esophagus thereby increasing the certainty of correct endotracheal tube placement.

While the invention has been described with respect to a limited number of embodiments, it will be appreciated that many variations, modifications, and other applications of the invention can be made within the scope of the appended claims.

The invention claimed is:

1. A video laryngoscope system for assisting tracheal intubation of a patient, the video laryngoscope system comprising:
   (a) a video laryngoscope including:
      i) a laryngoscope handle,
      ii) a laryngoscope blade configured for insertion into a patient's airway passage, the laryngoscope blade transversely extending from said laryngoscope handle and having a distal laryngoscope blade tip remote from said laryngoscope handle, an underside blade surface for intimate contact with a patient's tongue, and an upperside blade surface opposite said underside blade surface, said upperside blade surface having a stepped construction defining an elongated guide channel for supporting an endotracheal tube, and
      iii) an image capture module including an imaging unit daisy chain mounted on an exterior surface of the stepped construction of the laryngoscope blade and comprising at least two stationary imaging units each having a forward Field of View (FOV) toward a direction of insertion of the laryngoscope blade into the patient's airway passage to assist orienting a location of the laryngoscope blade tip in the patient's airway passage and recognizing intubation landmarks during insertion of the laryngoscope blade into the patient's airway passage, the imaging units being spaced apart longitudinally along said laryngoscope blade relative to said distal laryngoscope blade tip such that said image capture module includes a leading imaging unit proximate said distal laryngoscope blade tip and a trailing imaging unit behind said leading imaging unit relative to said distal laryngoscope blade tip,
      each said imaging unit capable of capturing a real-time video stream of the patient's airway passage during a manipulation of said laryngoscope blade therealong from an initial blade insertion into the patient's mouth to a final blade position,
      said trailing imaging unit capable of capturing a different real-time video stream of the patient's airway passage than said leading imaging unit at a location of said laryngoscope blade along the patient's airway passage,
      wherein said leading imaging unit and said trailing imaging unit have a non-overlapping Field Of View (FOV) arrangement, and
   (b) a controller for enabling a clinician performing an intubation to select at least one said real-time video stream during the intubation for real-time display on a display screen to assist intubation of the patient.

2. The system according to claim 1 wherein said trailing imaging unit is at least 1 cm behind said leading imaging unit relative to said distal laryngoscope blade tip.

3. The system according to claim 1 wherein said controller includes finger operated controls on said video laryngoscope for enabling a clinician performing an intubation to select said at least one real time video stream during the intubation for display on said display screen.

4. The system according to claim 1, further including a video stylet, wherein said controller is configured to enable a clinician performing an intubation to select at least one said real-time video stream from said image capture module and said video stylet during the intubation for real-time display on a display screen to assist intubation of the patient.

5. The system according to claim 1 wherein said stepped construction includes a major blade surface parallel and opposite said underside blade surface, an upright blade surface generally perpendicular to said major blade surface and an uppermost blade surface generally parallel to said major blade surface and tapering theretowards, said at least two stationary imaging units being spaced apart along said upright blade surface.

6. The system according to claim 1 wherein said stepped construction includes a major blade surface parallel and opposite said underside blade surface, an upright blade surface perpendicular to said major blade surface and an uppermost blade surface parallel to said major blade surface and tapering theretowards, said at least two stationary imaging units being spaced apart along said uppermost blade surface.

7. The system according to claim 1, wherein the display screen is provided onboard the laryngoscope handle.

8. The system according to claim 1, wherein the display screen is remote from the video laryngoscope and configured to simultaneously display two different real-time video streams captured by two different imaging units.

9. The system according to claim 1, wherein each imaging unit includes an illumination source and a digital imaging sensor.

10. A video laryngoscope system for assisting tracheal intubation of a patient, the video laryngoscope system comprising:
   a video laryngoscope including a laryngoscope handle, a laryngoscope blade transversely extending from the laryngoscope handle, and an image capture module mounted on the laryngoscope blade, the image capture module including a leading imaging unit and a trailing imaging unit configured to independently and simultaneously generate a real-time video stream of a patient's airway passage during the tracheal intubation for selective display on a display screen;
   a controller configured to control operation of the image capture module;
   the laryngoscope blade including an underside blade surface configured to deploy against the patient's tongue on insertion of the laryngoscope blade into the patient's mouth, and an upperside blade surface opposite the underside blade surface and having a stepped configuration defining an elongated guide channel configured to support an endotracheal tube during intubation;
   the upperside blade surface including a major blade surface parallel and opposite the underside blade surface, an upright blade surface generally perpendicular to the major blade surface, and an uppermost blade surface generally parallel to the major blade surface, said leading and trailing imaging units spaced apart on the upright blade surface; and
   the leading and trailing imaging units each having a forward Field Of View (FOV) during insertion of the laryngoscope blade into the patient's airway passage,
   wherein said leading imaging unit and said trailing imaging unit have a non-overlapping Field Of View (FOV) arrangement, and
   wherein the leading imaging unit is configured to obtain a view of the patient's vallecula region and the trailing imaging unit is configured to obtain a view of the patient's uvula and posterior pharynx during initial blade insertion into the patient's mouth.

11. The system according to claim 10, wherein said controller includes finger operated controls on said video laryngoscope for enabling a clinician performing an intubation to select said at least one real time video stream during the intubation for display on said display screen.

12. The system according to claim 10, further including a video stylet, wherein said controller is configured to enable a clinician performing an intubation to select at least one said real-time video stream from said image capture module and said video stylet during the intubation for real-time display on a display screen to assist intubation of the patient.

13. The system according to claim 10, wherein the display screen is configured to simultaneously display two different real-time video streams captured by two different imaging units.

14. A video laryngoscope system for assisting tracheal intubation of a patient, the video laryngoscope system comprising:

a video laryngoscope including a laryngoscope handle, a laryngoscope blade transversely extending from the laryngoscope handle, and an image capture module mounted on the laryngoscope blade, the image capture module including a leading imaging unit and a trailing imaging unit configured to independently and simultaneously generate a real-time video stream of a patient's airway passage during the tracheal intubation for selective display on a display screen;

a controller configured to control operation of the image capture module;

the laryngoscope blade including an underside blade surface configured to deploy against the patient's tongue on insertion of the laryngoscope blade into the patient's mouth, and an upperside blade surface opposite the underside blade surface and having a stepped configuration defining an elongated guide channel configured to support an endotracheal tube during intubation;

the upperside blade surface including a major blade surface parallel and opposite the underside blade surface, an upright blade surface generally perpendicular to the major blade surface, and an uppermost blade surface generally parallel to the major blade surface, said leading and trailing imaging units spaced apart on the uppermost blade surface; and the leading and trailing imaging units each having a forward Field Of View (FOV) during insertion of the laryngoscope blade into the patient's airway passage, wherein said leading imaging unit and said trailing imaging unit have a non-overlapping Field Of View (FOV) arrangement, and wherein the leading imaging unit is configured to obtain a view of the patient's vallecula region and the trailing imaging unit is configured to obtain a view of the patient's uvula and posterior pharynx during initial blade insertion into the patient's mouth.

15. The system according to claim 14, wherein said controller includes finger operated controls on said video laryngoscope for enabling a clinician performing an intubation to select said at least one real time video stream during the intubation for display on said display screen.

16. The system according to claim 14, further including a video stylet, wherein said controller is configured to enable a clinician performing an intubation to select at least one said real-time video stream from said image capture module and said video stylet during the intubation for real-time display on a display screen to assist intubation of the patient.

17. The system according to claim 14, wherein the display screen is configured to simultaneously display two different real-time video streams captured by two different imaging units.

* * * * *